(12) United States Patent
Aksakal

(10) Patent No.: US 8,475,475 B2
(45) Date of Patent: Jul. 2, 2013

(54) REMOTE CONTOL MECHANISM FOR AN ATRAUMATIC SURGICAL NEEDLE

(76) Inventor: Orhan Seyfi Aksakal, Ankara (TR)

( * ) Notice: Subject to any disclaimer, the term of this patent is extended or adjusted under 35 U.S.C. 154(b) by 165 days.

(21) Appl. No.: 12/990,856

(22) PCT Filed: Jun. 5, 2009

(86) PCT No.: PCT/TR2009/000070
§ 371 (c)(1),
(2), (4) Date: Nov. 3, 2010

(87) PCT Pub. No.: WO2009/148415
PCT Pub. Date: Dec. 10, 2009

(65) Prior Publication Data
US 2011/0082469 A1    Apr. 7, 2011

(30) Foreign Application Priority Data
Jun. 6, 2008  (TR) ................. 2008/04140

(51) Int. Cl.
*A61B 17/04*    (2006.01)

(52) U.S. Cl.
USPC .......................................... 606/144; 606/139

(58) Field of Classification Search
USPC ............... 606/139, 144, 145, 147, 148, 205, 606/207, 208, 222, 223, 224, 1; 600/104
See application file for complete search history.

(56) References Cited

U.S. PATENT DOCUMENTS

| | | | | |
|---|---|---|---|---|
| 2,646,045 A | * | 7/1953 | Priestley | 606/144 |
| 3,090,386 A | * | 5/1963 | Curtis | 606/146 |
| 6,146,392 A | * | 11/2000 | Smith | 606/147 |

* cited by examiner

*Primary Examiner* — Corrine M McDermott
*Assistant Examiner* — Robert A Lynch
(74) *Attorney, Agent, or Firm* — John Alumit

(57) ABSTRACT

The invention is a device for performing remote suturing operations with an atraumatic needle when there is distance between the hand and the place to be sutured. The device, which is adaptable to needles of different sizes used for surgical suturing, utilizes needle thrusting and needle capture mechanisms. These mechanisms allow the needle to pass through the tissue (flesh) and to be captured and released with a single stitch movement.

6 Claims, 5 Drawing Sheets

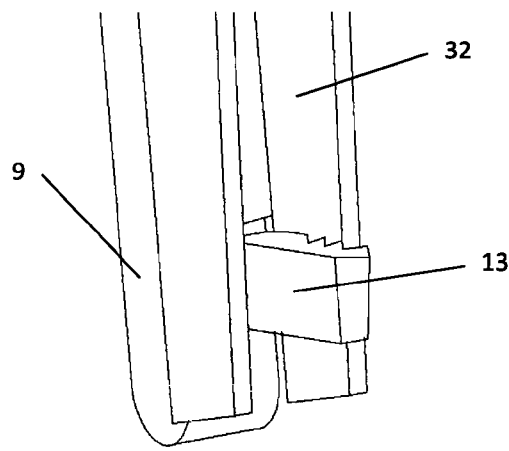
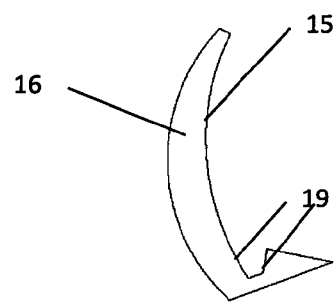
Figure 11
Figure 12
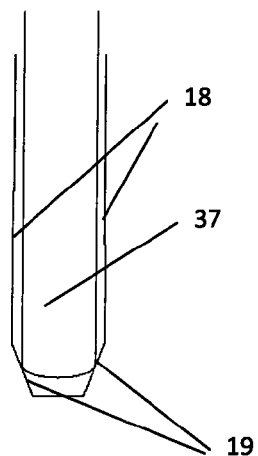
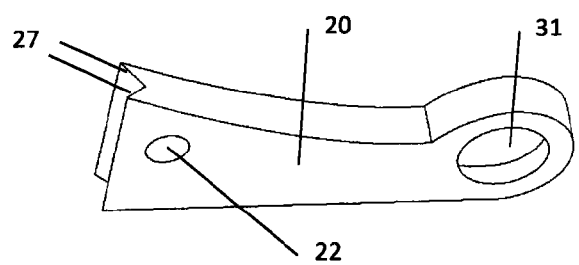
Figure 13
Figure 14

US 8,475,475 B2

REMOTE CONTOL MECHANISM FOR AN ATRAUMATIC SURGICAL NEEDLE

CROSS-REFERENCE TO RELATED APPPLICATION

This application claims the benefit of the priority filing date in PCT/TR2009/000070 and referenced in WIPO Publication WO/2009/148415. The earliest priority date claimed is Jun. 6, 2008.

FEDERALLY SPONSORED RESEARCH

None

SEQUENCE LISTING OR PROGRAM

None

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

1. Technical Field

The invention relates to devices used for deep suturing or laparoscopic suturing in which there is distance between the hand that moves the needle and the place to be sutured. The invention is a hand held device whose needle slot is adapted for different size needles and is designed to grip the needle so that it may pass through tissue (flesh) and be captured. All this is done by a single movement of the fingers holding the device.

There is no such mechanism used for the atraumatic surgical needles which are present in the market and currently in use.

The invention aims to solve the following technical problems: In current conditions of deep suturing or laparoscopic suturing, needles are not fixed in a needle slot. So the needle totters, especially if they are thin. This makes it difficult to find the target to be sutured, creating a risk that the needle may accidentally fall. Moreover, currently used devices that move the needle and that fix the needle are separately controlled. This may cause distraction for a surgeon in performing difficult operations. The invention will perform both movements (i.e., moving the needle and fixing the needle) at the same time, making it easier to manipulate the needle. This will limit the risk of distraction and tottering, and will speed up the operation.

Accordingly, the invention is realized in the form of a remote control mechanism with a needle slot adapted for various size needles that tighlty fixes the needle, thereby preventing thin needles from tottering in the slot, and allowing the needle to pass through tissue (flesh) and then be captured and released with a single hand movement (i.e., a single push of a surgeon's thumb).

SUMMARY

The invention relates to a remote control mechanism for an atraumatic surgical needle in which there is distance between the hand and the place to be sutured, thus allowing the needle to pass through the tissue (flesh), to be captured and released with a single stitch movement and which is also adaptable to needles of different sizes used for surgical suturing.

The invention jas the minimal components for performing remote suturing operations comprising a body, a handle fixed to the body, a needle slot thrusting handle, a pivot point for the needle slot thrusting handle, a control rod for the needle slot, a needle slot, a needle slot control rod hole, a needle slot pivot point, a control handle for a needle capture grip, a pivot point for the control handle for a needle capture grip, a control rod for a needle capture grip, a plurality of needle capture grips, a lock mechanism for the control handle for a needle capture grip, a plurality of clamp side supports, a needle channel, a back side of the needle channel, a front side of the needle channel, side walls for the needle channel, a conical shaped needle channel bottom, a needle clamp, a needle clamp slot, a spring hole, at least one spring, a spring pivot point shaft, a body extension side, at least one spring window, at least one curved needle clamp side, a needle channel opening wire, at least one clamp control part, a clamp connection rod, a clamp connection hole, a needle channel opener handle, a needle channel opener handle pivot point, a release button for the needle channel, a needle channel opener handle spring, and a lock mechanism hole.

DRAWINGS

PART NUMBERS

Figure 1:
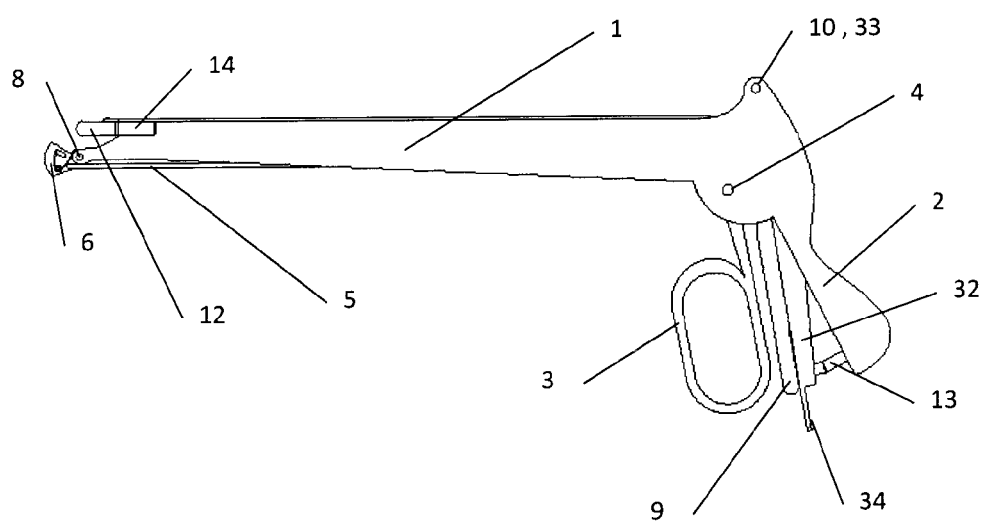
FIG. 1—Section view
FIG. 2—Section internal view
FIG. 3—Needle slot external side view
FIG. 4—Needle is in slot but not fixed
FIG. 5—Needle is in slot and clamp is thrusting
FIG. 6—Spring oblique
FIG. 7—Needle capture handle
FIG. 8—Needle capture grips are open
FIG. 9—Needle capture grips fixed the needle
FIG. 10—Needle capture handle detail—lock window
FIG. 11—The connection between needle capture and needle clamp handles
FIG. 12—The conical structure of the needle channel—side view
FIG. 13—The conical structure of the needle channel—front and rear
FIG. 14—Needle clamp tilted sides
FIG. 15—The relation between the needle clamp and the needle
FIG. 16—The connection between the clamp and the control parts—top plan view
FIG. 17—The connection between the clamp and the control parts—oblique
FIG. 18—End parts connection—top plan view
Figure 2:
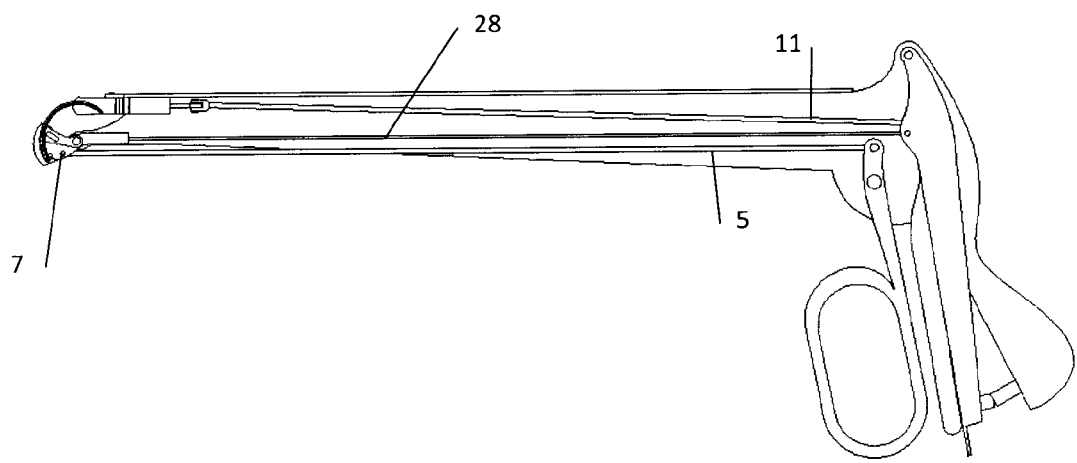
Figure 3:
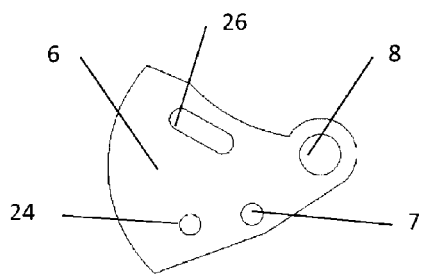
Figure 4:
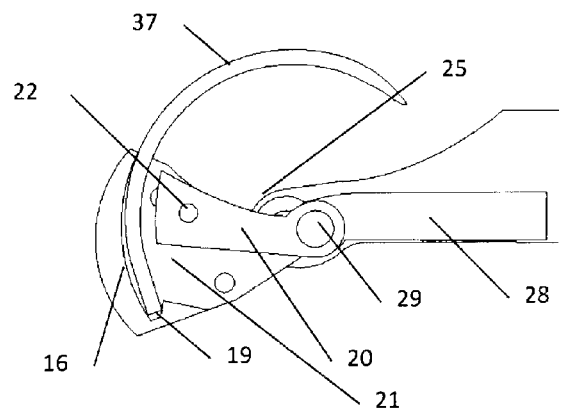

1-Body
2-A handle fixed to the body
3-Needle slot thrusting handle
4-Pivot point for the needle slot thrusting handle
5-Control rod for the needle slot
6-Needle slot
7-Hole for the needle slot control rod
8-Pivot point for the needle slot
9-Control handle for needle capture grip (jaws)
10-Pivot point of control handle for needle capture grip (jaws)
11-Control rod for needle capture grip 12-Needle capture grips
13-lock mechanism of the control handle for needle capture grip
14-Clamp side supports
15-Needle channel
16-Back side of the needle channel
17-Front side of needle channel
18-Side walls for the needle channel
19-Conical shaped needle channel bottom
20-Needle clamp
21-Needle clamp slot
22-Spring hole
23-Spring
24-Spring pivot point shaft
25-The side of body extension
26-Spring window (aperture)
27-Curved needle clamp sides
28-Needle channel opening wire
29-Clamp control parts
30-Clamp connection rod
31-Clamp connection hole
32-Needle channel opener handle
33-Needle channel opener handle pivot point
34-Release button for the needle channel
35-Needle channel opener handle spring
36-Lock mechanism hole
37-Needle

DETAILED DESCRIPTION

Referring to FIGS. 1-18, the invention comprises a body (1), a handle fixed to the body (2), a needle slot thrusting handle (3), a pivot point for the needle slot thrusting handle (4), a control rod for the needle slot (5), a needle slot (6), a needle slot control rod hole (7), a needle slot pivot point (8), a control handle for needle capture grip (9), a pivot point of control handle for needle capture grip (10), a control rod for needle capture grip (11), needle capture grips (12), a lock mechanism of the control handle for needle capture grip (13), clamp side supports (14), a needle channel (15), a back side of the needle channel (16), a front side of the needle channel (17), side walls for the needle channel (18), a conical shaped needle channel bottom (19), a needle clamp (20), a needle clamp slot (21), a spring hole (22), a spring (23), a spring pivot point shaft (24), the side of body extension (25), a spring window (26), curved needle clamp sides (27), a needle channel opening wire (28), clamp control parts (29), a clamp connection rod (30), a clamp connection hole (31), a needle channel opener handle (32), a needle channel opener handle pivot point (33), a release button for the needle channel (34), a needle channel opener handle spring (35), a hole of lock mechanism (36). The front side of the needle channel (17) is a virtual component and represents the needle clamp side of the needle channel. The needle channel opener handle spring (35) is placed between the handle fixed to the body (2) and needle channel opener handle (32), and is a pushing spring.

Referring to FIG. 1, the body (1) connects the controls and the needle in a remote control mechanism for an atraumatic needle. The body can also be made circular and be passed through a laparoscopic trocar. The body length can be extended on demand so that suture control distance would be longer.

A User controls the tool by a handle fixed to the body (2). Other systems are assembled on these two main components (body and mounted handle) by their functions. The needle slot thrusting handle (3) is movable back and forth in the Pivot point for the needle slot thrusting handle (4).

This movement is transferred to the control rod in the needle slot that is mounted to the other side, and by means of that rod, to the needle slot (6). The intersection point is the needle slot control rod hole (7). See FIGS. 1-2.

The needle slot, with back and forth movements of the control rod, performs circular movements on the needle slot pivot point (when the handle is pulled back to the mounted handle, the needle slot moves forward.)

Figure 7:
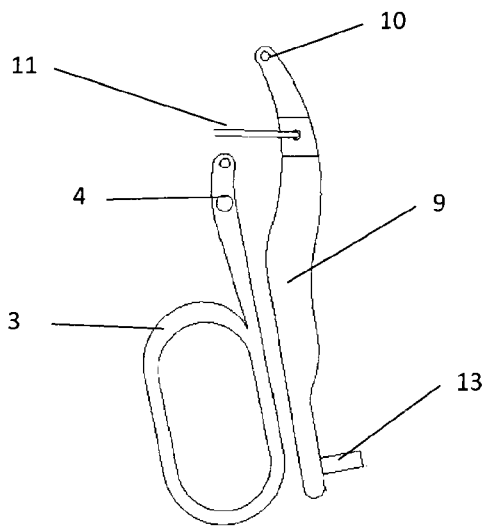
Figure 8:
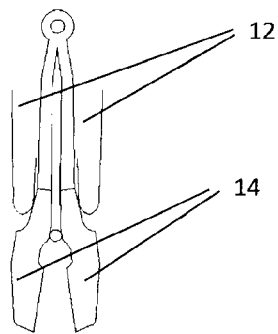
Figure 9:
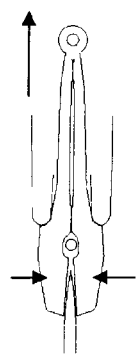
Figure 10:
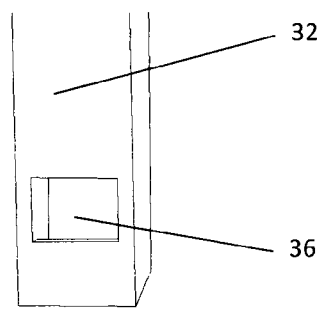
Figure 15:
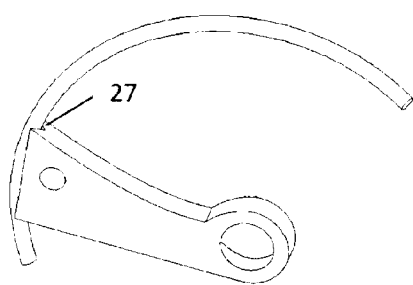
Figure 16:
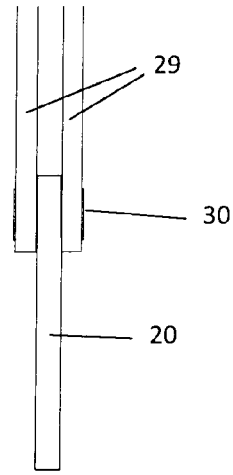
Figure 17:
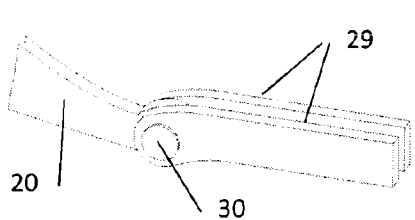
Figure 18:
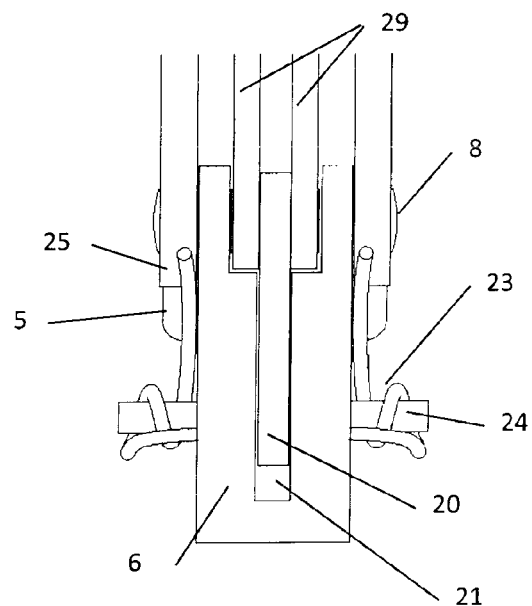

Referring to FIGS. 1 and 7-8, the control handle for the needle capture grip (9) is linked to the handle fixed to the body by a pivot point (10) and performs back-forth movements on that pivot point.

These movements are transferred to the control handle for the needle capture grip (9) (located between the pivot point and the other side of the handle), the control rod for the needle capture grip (11), and the needle capture grips (12) control mechanism.

Therefore when this control handle for the needle capture grip (9) moves to the mounted handle (2), the control rod for the needle capture grip (11) is pulled and the needle capture grips (12) approach each other to catch the needle. The needle capture grips are positioned in such a way as to receive the needle in-between, after the needle comes out of the tissue.

When the rod is pulled (the handle is pressed) the grips approach each other with the aid of the clamp side supports and squeezes the needle. Control of the control rod for the needle capture grip is done by the needle slot thrusting handle (3).

When the control rod for the needle capture grip approaches the body with the help of the finger (the needle is placed between the grips), the control rod for the needle capture grip is pressed in the last 1 cm of movement in the direction of the handle fixed to the body.

When closely approached, a lock mechanism at the end of the the control rod for the needle capture activates and fixes the needle between the grips. Without pressing a second time, the lock mechanism cannot activate.

When the needle capture grips are pulled towards the handle, they approach each other with the help of the clamp side supports (14) and squeeze the needle.

Figure 5:
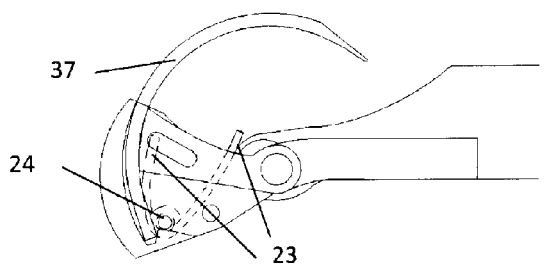
Figure 6:
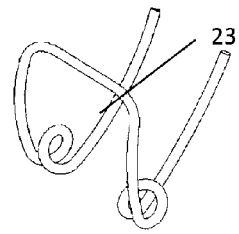

Referring to FIG. 5, the grips have a spring (23) mechanism from the middle to the outer sides. When the middle is pushed forward, the outer sides seperate and evolve into a position that receives the needle in between.

Referring to FIGS. 1, 4, 12-13, needle is in the needle slot (6) which is also in the needle channel (15). The front side of the needle channel (17) (back side of the body) is also designed in accordance with the pitch of the needle. The front side (17) is mainly composed of the needle clamp (20). The side walls for the needle channel (18) is a little bit wider than the needle in order to allow the needle to freely move when it enters and exits the channel. The last standing point of the needle from either front to back, or from sides to bottom, is conical shaped (19) and is aimed to adapted to the different sizes of needles.

Referring to FIGS. 1, 3-6, 12, 14, 16-18, the needle clamp is under the control of the spring (23) with the help of the spring hole (22). The spring pivot point shaft (24) is near the conical shaped needle channel bottom and near the needle body. The place where the spring takes its strength is the side of body extension (25). The spring gets pressed here and pushes the clamp (20) towards the needle. This movement of the needle clamp takes place in the needle clamp slot located in the needle slot (21). The movement of the spring that coincides with the channel occurs in the spring window (26). The top and bottom sides of the needle clamp touching the needle are tilted internally in order to grip the needle (27). The hardness of the spring is adjusted so that it does not allow the needle to move to the right or left. The spring, in the normal position, is arranged to push the needle behind the channel (16). The movement of the clamp (that is away from the needle and allows the channel for taking off the needle to be released) is provided by the needle channel opening wire (28). There are two parts for taking the clamp in from both sides at the end of the wire (29). The clamp connection rod (30) provides the connection between the two parts and the clamp. With the help of this rod, those parts in both sides and the clamp are connected. However, the clamp connection hole (31) has flexibility for permitting the clamp to make a full circular movement. The parts that supply the connection to the rod on both sides of the clamp are connected to the needle channel opening wire (28) rigidly. This wire reaches through the body to the handle and is mounted near the middle section of the needle channel opener handle (32). This handle could move back and forth over the needle channel opener handle Pivot point (33). Therefore, when the release button for the needle channel (34) is pressed towards the handle fixed to the body, the needle clamp is pulled away from the needle and the needle is allowed to be placed into the channel. The needle channel opener handle is pushed away from the handle fixed to the body with the help of the needle channel opener handle spring (35). This helps with the correct positioning upon first usage. The needle channel opener handle is positioned between (2) the handle fixed to the body and the control handle for the needle capture grip (9). There is a lock mechanism hole (36) in the handle made from corrugated sheet which allows the lock mechanism to work freely (13). The reason why this mechanism is adjusted in such a way is to allow the needle to be passed through the tissue (flesh), and to be captured and released with a single stitch movement by effective working of the grips. When the release button for the needle channel (34) (located at the end of the needle channel opener handle) is pressed once in the direction of the handle fixed to the body; the needle channel is opened and can be utilized for needle use.

APPLICATION OF THE INVENTION

Referring to FIGS. 1-2, 4 and 12, the device, which is a needle control mechanism upon which a needle is mounted, is handled by using the handle (2) fixed to the body (1). At the starting position, the lock mechanism of the control handle for the needle capture grip (13) is not used and it is pushed forward by the needle channel opener handle (32) by the needle channel opener handle spring (35). In this way, the needle capture grips (12) are opened and ready to receive the needle in between. Also in this way, the needle clamp (20) is already available. To place the needle in its place, the needle slot thrusting handle (3) is pulled midway. in this position, control of needle channel from the handle is more effective. To place the needle into the channel, the release button for the needle channel (34) is pressed towards the handle fixed to the body. This movement will thrust the needle clamp (20) through the needle channel opening wire (28), clamp control parts (29) and clamp connection rod. The needle clamp is pulled to the body making a channel for the needle to be received. The needle is pushed towards to the channel from its sutured side. When the needle is placed, the button is released. With the help of a strong spring (23), the needle clamp is pushed towards the needle and the needle is clamped. The device is ready to use. Depending on the operation, the device is taken to the proximity of the suture area through a pipe or directly. A surgeon directs the needle to the tissue by pulling the needle slot thrusting handle (3) towards the handle fixed to the body. When slot thrusting handle (3) approaches the handle fixed to the body, it pulls the needle channel opener handle (32) with it. At the same time, the grips approach the needle that is already placed in between, and the needle clamp releases the needle. At the final position, the lock mechanism activates and the needle is fixed between the grips. Thus, the needle passes through the tissue and is caught at the same time. The needle slot thrusting handle is pushed away from the handle fixed to the body. Thus, the needle is released from the channel. With the help of the lock mechanism, the needle is discarded and unchanged. When the needle slot thrusting handle is pushed away totally, the needle is released from the channel (15) and tissue, and is prepared for a second suture. In this stage, the needle is fixed in the grips at the end, the lock mechanism at the handle is activated, and the channel is open. When the needle slot thrusting handle (3) is pulled again, the part of the needle with the suture again enters the channel. At the last stage, the needle is place in the channel perfectly. The lock mechanism has such a construction that it stops functioning when it hits a final point, so that the needle capture grips are freed and opened. At the same time, the clamp is also freed from the lock, and moves back and forth to squeeze the needle. The device is ready for another suturing.

The invention claimed is:

1. A remote control mechanism for an atraumatic surgical needle for performing remote suturing operations, the mechanism comprising:
   a. an elongated hollow body with a first and second end, a handle fixed to the body extending distally at the first end of the body and a needle channel and needle capture grips at the second end of the body;
   b. a needle slot thrusting handle extending distally from the body and parallel to the handle fixed to the body is affixed on a pivot point, the pivot point allowing the needle slot thrusting handle to rotate towards the handle fixed to the body and advance a control rod for a needle slot towards the second end of the body;
   c. a needle slot is affixed at the second end of the body on a needle slot pivot point and to the control rod by a needle slot control rod hole, the needle slot being capable of moving back and forth in a circular movement;
   d. a control handle for a needle capture grip extends distally from the body on a pivot point, the pivot point allowing the control handle to rotate towards the handle fixed to the body and pull a control rod for a needle capture grip towards the first end of the body;
   e. a plurality of needle capture grips to receive a needle after passage through tissue are affixed to the control rod for the needle capture grip and include a plurality of clamp side supports, the needle capture grips and clamp side supports moving towards each other when the control handle for a needle capture grip is pulled towards the handle fixed to the body;
   f. a lock mechanism extends from the control handle for a needle capture grip to the handle fixed to the body and is activated when the control handle for a needle capture grip approaches the handle fixed to the body , fixing the needle between the needle capture grips;
   g. the needle slot is within a needle channel comprising a back side, a front side, side walls, and a conical shaped needle channel bottom; and
   h. a needle clamp, attached to at least one clamp control part by a clamp connection through rod, comprises the front side of the needle channel and includes a needle clamp slot, the needle clamp under the control of at least one spring mounted on a spring pivot point shaft through a spring hole, the spring being supported by a body extension side is pressed and pushes the needle clamp towards a needle in the needle slot as seen through at least one spring window through the needle slot.

2. The remote control mechanism for an atraumatic surgical needle as set forth in claim 1, whereby the needle channel opener handle is connected to the first end the body and may be turned over the needle channel opener handle pivot point, and the point at which the needle channel opening wire is assembled is located between the pivot point and the second end of the handle, making it possible to pull the needle channel opening wire and clamp control parts to the first end in the direction in which the triggering clamp connection rod and clamp connection hole are mounted, by pressing the handle fixed to the body.

3. The remote control mechanism for an atraumatic surgical needle as set forth in claim 1, whereby the needle clamp may be turned over the point with the clamp control parts which affects the clamp connection rod located in the clamp connection hole.

4. The remote control mechanism for an atraumatic surgical needle as set forth in claim 1, whereby a release button is provided for the needle channel located at the extension of the needle channel opener handle allowing the lock mechanism for the needle capture grip to be released through a lock mechanism hole in the needle channel opener.

5. A remote control mechanism for an atraumatic surgical needle as set forth in claim 1, wherein a needle channel opener handle is located at the first end of the body between the handle fixed to body and the control handle for the needle capture grip, thus allowing the lock mechanism to work independently with the help of the lock mechanism hole, at the same time permitting the needle channel to be opened to access the needle as the needle channel moves independently towards the handle fixed to the body.

6. The remote control mechanism for an atraumatic surgical needle as set forth in claim 1, wherein the needle capture grips handle and the needle channel opener handle are placed respectively between the needle slot thrusting handle and the handle fixed to the body to enable the handling of all handles in accordance with movement of the needle slot thrusting handle whereby, when the needle slot thrusting handle approaches the handle fixed to the body, it takes the other two handles in the direction of the handle fixed to the body so that when the needle passes slightly through the flesh, the needle clamp grips first take action and fix the needle rigidly, thus allowing the needle channel to be opened for the exit and entrance of the needle into the needle channel through its rear end.

* * * * *